US009352052B2

(12) United States Patent
Kobayashi

(10) Patent No.: US 9,352,052 B2
(45) Date of Patent: May 31, 2016

(54) RETROGRADE TRANSPORT VIRAL VECTOR SYSTEM HAVING ENVELOPE COMPRISING FUSED GLYCOPROTEIN

(75) Inventor: Kazuto Kobayashi, Fukushima (JP)

(73) Assignee: JAPAN SCIENCE AND TECHNOLOGY AGENCY, Kawaguchi-Shi, Saitama (JP)

( * ) Notice: Subject to any disclaimer, the term of this patent is extended or adjusted under 35 U.S.C. 154(b) by 206 days.

(21) Appl. No.: 13/511,873

(22) PCT Filed: Nov. 11, 2010

(86) PCT No.: PCT/JP2010/070136
§ 371 (c)(1),
(2), (4) Date: Aug. 1, 2012

(87) PCT Pub. No.: WO2011/068019
PCT Pub. Date: Jun. 9, 2011

(65) Prior Publication Data
US 2012/0295964 A1    Nov. 22, 2012

(30) Foreign Application Priority Data

Dec. 2, 2009    (JP) .................................. 2009-274156

(51) Int. Cl.
| C07H 21/04 | (2006.01) |
| A01N 63/00 | (2006.01) |
| A61K 48/00 | (2006.01) |
| C07K 14/005 | (2006.01) |
| C12N 15/86 | (2006.01) |

(52) U.S. Cl.
CPC ........... *A61K 48/0075* (2013.01); *C07K 14/005* (2013.01); *C12N 15/86* (2013.01); *C12N 2740/16045* (2013.01); *C12N 2740/16052* (2013.01); *C12N 2760/20122* (2013.01); *C12N 2760/20222* (2013.01); *C12N 2810/6081* (2013.01)

(58) Field of Classification Search
None
See application file for complete search history.

(56) References Cited

U.S. PATENT DOCUMENTS

| 6,818,209 | B1 * | 11/2004 | Mitrophanous et al. | ..... 424/93.2 |
| 7,238,672 | B1 * | 7/2007 | Jacob et al. | ................. 514/44 R |
| 2003/0026791 | A1 * | 2/2003 | Humeau et al. | ............ 424/93.21 |
| 2003/0124146 | A1 | 7/2003 | Schnell et al. | |
| 2004/0071675 | A1 | 4/2004 | Mazarakis et al. | |

FOREIGN PATENT DOCUMENTS

| EP | 2 508 599 A1 | 10/2012 |
| JP | 2004-517057 A | 6/2004 |
| JP | 2009-34029 A | 2/2009 |

OTHER PUBLICATIONS

Whitt et al. Membrane Fusion Activity, Oligomerization, and Assembly of the Rabies Virus Glycoprotein. Virology, 1991. 185:681-688.*
Sanders, David Avram. No False Start for Novel Pseudotyped vectors. Current Opinion in Biotechnology, 2002. 13:437-442.*
Kato et al. Neuron-Specific Gene Transfer Through Retrograde Transport of Lentiviral Vector Pseudotyped with a Novel Type of Fusion Envelope Glycoprotein, Human Gene Therapy, 22(12): 1511-1523.*
Gaudin et al. Rabies virus-induced Membrane Fusion, Molecular Membrane Biology, 1999. 16:21-31.*
Kato, S. et al., "Efficient Gene Transfer via Retrograde Transport in Rodent and Primate Brains Using a Human Immunodeficiency Virus Type 1-Based Vector Pseudotyped with Rabies Virus Glycoprotein", Human Gene Therapy, Nov. 2007, vol. 18, No. 11, pp. 1141-1152 (Abstract only).
Kato, S. et al., "Neuron-Specific Gene Transfer Through Retrograde Transport of Lentiviral Vector Pseudotyped with a Novel Type of Fusion Envelope Glycoprotein", Human Gene Therapy, Dec. 2011, vol. 22(12), pp. 1511-1523 (Abstract only).
Kitagawa, R. et al., "Differential characteristics of HIV-based versus SIV-based lentiviral vector systems: Gene delivery to neurons and axonal transport of expressed gene," Neuroscience Research, 2007, pp. 550-558, vol. 57.
Desmaris, N. et al., "Production and Neurotropism of Lentivirus Vectors Pseudotyped with Lyssavirus Envelope Glycoproteins," Molecular Therapy, Aug. 2001, pp. 149-156, vol. 4, No. 2.
Mazarakis, N. D. et al., "Rabies virus glycoprotein pseudotyping of lentiviral vectors enables retrograde axonal transport and access to the nervous system after peripheral delivery," Human Molecular Genetics, 2001, pp. 2109-2121, vol. 10, No. 19.
Foley, H. D. et al., "A recombinant rabies virus expressing vesicular stomatitis virus glycoprotein fails to protect against rabies virus infection," PNAS, Dec. 19, 2000, pp. 14680-14685, vol. 97, No. 26.
Morimoto, K. et al., "High level of expression of a human rabies virus-neutralizing monoclonal antibody by a rhabdovirus-based vector," Journal of Immunological Methods, 2001, pp. 199-206, vol. 252.
Mochizuki, H. et al., "High-Titer Human Immunodeficiency Virus Type 1-Based Vector Systems for Gene Delivery into Nondividing Cells," Journal of Virology, Nov. 1998, pp. 8873-8883, vol. 72, No. 11.

(Continued)

*Primary Examiner* — Christopher M Babic
*Assistant Examiner* — Kimberly A Aron
(74) *Attorney, Agent, or Firm* — Ping Wang; Andrews Kurth LLP

(57) ABSTRACT

Provided is a lentiviral vector system which sustains a high-frequency retrograde transportation ability in animal brain and has a higher titer. A kit for preparing a retrograde transport viral vector, which comprises: (1) a packaging plasmid containing the gag gene and pol gene of HIV-1; (2) a packaging plasmid containing an accessory gene of HIV-1; (3) a transfer plasmid containing a target gene; and (4) an envelope plasmid containing, as an envelope gene, a gene encoding a fused polypeptide comprising the extracellular domain of rabies virus glycoprotein (RV-G), the transmembrane domain of rabies virus glycoprotein (RV-G) or vesicular stomatitis virus glycoprotein (VSV-G) and the intracellular domain of vesicular stomatitis virus glycoprotein (VSV-G).

15 Claims, 5 Drawing Sheets

(56) References Cited

OTHER PUBLICATIONS

English-language translation of International Search Report issued in International Patent Application No. PCT/JP2010/070136, mailed Dec. 21, 2010.

Kordower, J. H. et al., "Neurodegeneration Prevented by Lentriviral Vector Delivery of GDNF in Primate Models of Parkinson's Disease," Science, Oct. 2000, pp. 767-773, vol. 290.

Marr, R. A., et al., "Neprilysin Gene Transfer Reduces Human Amyloid Pathology in Transgenic Mice," The Journal of Neuroscience, Mar. 15, 2003, pp. 1992-1996, vol. 23, No. 6.

Rosenblad, C. et al., "Long-term striatal overexpression of GDNF selectively downregulates tyrosine hydroxylase in the intact nigrostriatal dopamine system," European Journal of Neuroscience, Jan. 2003, pp. 260-270, vol. 17.

Lo Bianco, C. et al., "Lentiviral vector delivery of parkin prevents dopaminergic degeneration in an α-synuclein rat model of Parkinson's disease," PNAS, Dec. 14, 2004, pp. 17510-17515, vol. 101, No. 50.

Naldini, L. et al., "Efficient transfer, integration, and sustained long-term expression of the transgene in adult rat brains injected with a lentiviral vector," Proc. Natl. Acad. Sci., Oct. 1996, pp. 11382-11388, vol. 93.

Reiser, J. et al., "Transduction of nondividing cells using pseudotyped defective high-titer HIV type 1 particles," Proc. Natl. Acad. Sci., Dec. 1996, pp. 15266-15271, vol. 93.

Mitrophanous, K. A. et al., "Stable gene transfer to the nervous system using a non-primate lentiviral vector," Gene Therapy, 1999, pp. 1808-1818, vol. 6.

Azzouz, M. et al., "VEGF delivery with retrogradely transported lentivector prolongs survival in a mouse ALS model," Nature, May 27, 2004, pp. 413-417, vol. 429.

Supplementary European Search Report of International Application No. 10834471 mailed May 29, 2013.

Inoue, K. et al., "Efficient retrograde gene transfer into primate brain with an HIV-1 based lentiviral vector pseudotyped with rabies virus glycoprotein", Society for Neuroscience, vol. 38, 2008. (Abstract only).

Kuramochi, M. et al. "Highly efficient retrograde gene transfer system by a lentiviral vector pseudotyped with fusion envelope glycoprotein for the study of structure and function of neural circuit", Society for Neuroscience, vol. 40, 2010. (Abstract only).

Kato, S. et al., "A Lentiviral Strategy for Highly Efficient Retrograde Gene Transfer by Pseudotyping with Fusion Envelope Glycoprotein", Human Gene Therapy, vol. 22, No. 2, Feb. 2011, pp. 197-206.

Supplementary European Search Report of Application No. 11843579.1 mailed Apr. 15, 2014.

Carpentier, D. C. J., et al., "Enhanced pseudotyping efficiency of HIV-1 lentiviral vectors by a rabies/vesicular stomatitis virus chimeric envelope glycoprotein", Gene Ther., Jul. 2012, vol. 19(7), pp. 761-774.

Schaffer, D. V., et al,, "Molecular engineering of viral gene delivery vehicles", Annual Review of Biomedical Engineering, 2008,vol. 10, pp. 169-194.

* cited by examiner

RETROGRADE TRANSPORT VIRAL VECTOR SYSTEM HAVING ENVELOPE COMPRISING FUSED GLYCOPROTEIN

BACKGROUND OF THE INVENTION

1. Technical Field

The present invention relates to a lentiviral vector system and a method of gene transfer and gene therapy using the viral vector system, wherein the viral vector system is pseudotyped by a viral vector having an excellent retrograde transport ability particularly in the brain and having high production efficiency, in particular, a fused polypeptide comprising an extracellular domain and a transmembrane domain of rabies virus glycoprotein (RV-G) and an intracellular domain of vesicular stomatitis virus glycoprotein (VSV-G)

2. Background Art

Non-proliferative (non-replicating) recombinant lentiviral vectors are used in a number of studies as a vector for gene therapy to treat various diseases, such as a system which transports a target gene to a non-dividing cell in the central nervous system (CNS) and maintains its expression over a long period of time (Nonpatent Literatures 1-4). In particular, a primate lentiviral vector from HIV-1 (human immunodeficiency virus type 1) is the most proven vector for gene therapy (Nonpatent Literatures 5-8).

On the other hand, for gene therapy of a certain cranial nerve disease, useful is a viral vector which can infect a nerve terminal, is retrogradely transported through an axon and introduce a target gene into a cell body in a target site located far from the infected site (FIG. 1).

To date, as an envelope glycoprotein (an envelope gene protein), a retrograde transport system in the brain of cynomolgus monkey was developed using a recombinant HIV-1 virus which uses (is pseudotyped by) a vesicular stomatitis virus (VSV) glycoprotein (VSV-G), but the retrograde transportation of the vector was not efficient (Nonpatent Literature 9). In the method described in the reference, very few cells in the central nervous system were retrogradely infected with the recombinant HIV-1 virus injected into the striatum of the monkey, as indicated by immunostaining.

On the other hand, rabies virus (RV) is known to have an activity that RV infects a synapse terminal, and is retrogradely transported through an axon. Indeed, there is a report that a retrograde transportation ability of a non-primate lentiviral vector based on equine anemia virus was promoted by RV-G (Nonpatent Literatures 10 and 11, and Patent Literature 1).

Further, HIV-1 lentivirus pseudotyped by RV-G has been reported (Nonpatent Literature 3), but, in that report, an animal experiment (in vivo) was not actually conducted using that viral vector. In addition, gene transfer in CNS with a HIV-1 vector pseudotyped by a glycoprotein from Mokola lyssavirus, a neurotropic virus causing rabies, or VSV-G has been studied. As a result of the nasal injection of the HIV-1 vector pseudotyped by the Mokola lyssavirus glycoprotein or VSV-G into a rat, these vectors were mutually comparable with regard to retrograde transportation to the olfactory nerve system (Nonpatent Literature 12). In addition, in that literature, an example in which a viral vector was administered through striatum was not described.

To date, the present inventors have revealed that highly-frequent retrograde gene transfer at various regions in the brain can be feasible by preparing a HIV-1 lentivirus vectors pseudotyped by rabies virus glycoprotein gene (RV-G) (RV-G/HIV-1 vector) (Patent Literature 2, Hum. Gene Ther., 2007).

REFERENCE LIST

Patent Literature
Patent Literature 1: National Publication of International Patent Application No. 2004-517057
Patent Literature 2: Japanese Patent Laid-Open No. 2009-34029
Non Patent Literature
Non-Patent Literature 1: NALDINI, L., BLÖMER, U., GAGE, F. H., TRONO, D., and VERMA, I. M. (1996). Efficient transfer, integration, and sustained long-term expression of the transgene in adult rat brains injected with a lentiviral vector. Proc. Natl. Acad. Sci. USA 93, 11382-11388.
Non-Patent Literature 2: REISER, J., HARMISON, G, KLUEPFEL-STAHL, S., BRADY, R. O., KARLSSON, S., and SCHUBERT, M. (1996). Transduction of nondividing cells using pseudotyped defective high-titer HIV type 1 particles. Proc. Natl. Acad. Sci. USA 93, 15266-15271.
Non-Patent Literature 3: MOCHIZUKI, H., SCHWARTZ, J. P., TANAKA, K., BRADY, R. O., and REISER, J. (1998). High-titer human immunodeficiency virus type 1-based vector systems for gene delivery into nondividing cells. J. Virol. 72, 8873-8883.
Non-Patent Literature 4: MITROPHANOUS, K. A., YOON, S., ROHLL, J. B., PATIL, D., WILKES, F. J., KIM, V. N., KINGSMAN, S. M., KINGSMAN, A. J., and MAZARAKIS, N. D. (1999). Stable gene transfer to the nervous system using a non-primate lentiviral vector. Gene Ther. 6, 1808-1818.
Non-Patent Literature 5: KORDOWER, J. H., EMBORG, M. E., BLOCH, J., MA, S. Y., CHU, Y., LEVENTHAL, L., MCBRIDE, J., CHEN, E.-Y., PALFI, S., ROITBERG, B. Z., BROWN, W. D., HOLDEN, J. E., PYZALSKI, R., TAYLOR, M. D., CARVEY, P., LING, Z., TRONO, D., HANTRAYE, P., DÉGLON, N., and AEBISCHER, P. (2000). Neurodegeneration prevented by lentiviral vector delivery of GDNF in primate models of Parkinson's disease. Science 290, 767-773.
Non-Patent Literature 6: MARR, R. A., ROCKENSTEIN, E., MUKHERJEE, A., KINDY, M. S., HERSH, L. B., GAGE, F. H., VERMA, I. M., and MASLIAH, E. (2003). Neprilysin gene transfer reduces human amyloid pathology in transgenic mice. J. Neurosci. 23, 1992-1996.
Non-Patent Literature 7: ROSENBLAD, C., GEORGIEVSKA, B., and KIRIK, D. (2003). Long-term striatal overexpression of GDNF selectively downregulates tyrosine hydroxylase in the intact nigrostriatal dopamine system. Eur. J. Neurosci. 17, 260-270.
Non-Patent Literature 8: LO BIANCO, C., SCHNEIDER, B. L., BAUER, M., SAJADI, A., BRICE, A., IWATSUBO, T., and AEBISCHER, P. (2004). Lentiviral vector delivery of parkin prevents dopaminergic degeneration in an α-synuclein rat model of Parkinson's disease. Proc. Natl. Acad. Sci. USA 101, 17510-17515.
Non-Patent Literature 9: KITAGAWA, R., MIYACHI, S., HANAWA, H., TAKADA, M., and SHIMADA, T. (2007). Differential characteristics of HIV-based versus SW-based lentiviral vector systems: gene delivery to neurons and axonal transport of expressed gene. Neurosci. Res. 57, 550-558.
Non-Patent Literature 10: MAZARAKIS, N. D., AZZOUZ, M., ROHLL, J. B., ELLARD, F. M., WILKES, F. J., OLSEN, A. L., CARTER, E. E., BARBER, R. D., BABAN, D. F., KINGSMAN, S. M., KINGSMAN, A. J., O'MALLEY, K., and MIIROPHANOUS, K. A. (2001). Rabies virus glycoprotein pseudotyping of lentiviral vectors enables retrograde axonal transport and access to the nervous system after peripheral delivery. Human Mol. Genet. 10, 2109-2121.

Non-Patent Literature 11: AZZOUZ, M., RALPH, G. S., STORKEBAUM, E., WALMSLEY, L. E., MITROPHANOUS, K. A., KINGSMAN, S. M., CARMELIET, P., and MAZARAKIS, N. D. (2004). VEGF delivery with retrogradely transported lentivector prolongs survival in a mouse ALS model. Nature 429, 413-417.

Non-Patent Literature 12: DESMARIS, N., BOSCH, A., SALAÜN, C., PETIT, C., PRÉVOST, M.-C., TORDO, N., PERRIN, P., SCHWARTZ, O., DE ROCQUIGNY, H., and HEARD, J. M. (2001). Production and neurotropism of lentivirus vectors pseudotyped with Lyssavirus envelope glycoproteins. Mol. Ther. 4, 149-156.

SUMMARY OF INVENTION

Technical Problem

The above RV-G/HIV-1 vector is an excellent system having a high retrograde transportation ability, but its production efficiency is low and the RV-G/HIV-1 vector may not be suitable for in vivo gene transfer experiments which require a high-titer stock of vectors.

Therefore, an object of the present invention is to provide a lentiviral vector system which sustains a retrograde transportation ability with higher efficiency, and has a higher titer (a functional titer) in the brain of an animal, including primate mammals.

Solution to Problem

The present inventor has found that a highly-frequent retrograde transportation ability comparable with, or equal or greater than that of the RV-G/HIV-1 vector can be achieved by pseudotyping a lentiviral vector using, as an envelope, a fused polypeptide comprising rabies virus glycoprotein (RV-G) at the N-terminus and vesicular stomatitis virus glycoprotein (VSV-G) at the C-terminus. At the same time, the present inventor has found that transfection efficiency into cells (a functional titer) can also be significantly improved. Accordingly, the present inventor has completed the present invention.

Examples can include a fused polypeptide comprising an extracellular domain of rabies virus glycoprotein (RV-G), a transmembrane domain of rabies virus glycoprotein (RV-G) or vesicular stomatitis virus glycoprotein (VSV-G) and an intracellular domain of vesicular stomatitis virus glycoprotein (VSV-G).

That is, the present invention relates to the following aspects.

[Aspect 1]
A kit for preparing a retrograde transport viral vector comprising:
(1) a packaging plasmid containing the gag gene and the pol gene of HIV-1;
(2) a packaging plasmid containing an accessory gene of HIV-1;
(3) a transfer plasmid containing an target gene (a transgene); and
(4) an envelope plasmid containing, as an envelope gene, a gene encoding a fused polypeptide comprising an extracellular domain of rabies virus glycoprotein (RV-G), a transmembrane domain of rabies virus glycoprotein (RV-G) or vesicular stomatitis virus glycoprotein (VSV-G) and an intracellular domain of vesicular stomatitis virus glycoprotein (VSV-G).

[Aspect 2]
A kit for preparing a viral vector according to the present invention, and a kit for preparing a producer cell including a host cell.

[Aspect 3]
A method of producing a producer cell, comprising: co-transfecting an infected cell with the packaging plasmid, the transfer plasmid, and the envelope plasmid, contained in the kit for preparing a viral vector according to the present invention.

[Aspect 4]
The producer cell obtained by the method of producing a producer cell according to the present invention.

[Aspect 5]
A method of producing a viral vector, comprising: culturing the producer cell according to the present invention and harvesting virus particles from the supernatant of the culture.

[Aspect 6]
A viral vector possessing a retrograde transportation ability, produced by the method of producing a viral vector according the present invention.

[Aspect 7]
A method of gene transfer, comprising: infecting a nerve terminal of an animal with the viral vector according to the present invention; introducing the viral vector into a cell body of the nerve at a target region in the brain by retrograde transportation of the viral vector through an axon of the nerve; and expressing a target gene in the cell body.

[Aspect 8]
An agent for gene therapy containing the viral vector according the present invention as an active ingredient.

[Aspect 9]
A method of gene therapy for a brain disease, comprising; integrating a target gene introduced by the method according to the present invention into the chromosome of a cell in a target region to express it.

[Aspect 10]
An envelope for pseudotyping a lentiviral vector, comprising an extracellular domain of rabies virus glycoprotein (RV-G), a transmembrane domain of rabies virus glycoprotein (RV-G) or vesicular stomatitis virus glycoprotein (VSV-G) and the intracellular domain of vesicular stomatitis virus glycoprotein (VSV-G)

[Aspect 11]
A gene encoding an envelope comprising the fused polypeptide according to Aspect 10.

[Aspect 12]
A envelope plasmid comprising the gene encoding an envelope comprising the fused polypeptide according to Aspect 11.

Advantageous Effect of the Invention

The present invention demonstrates, in vivo, that in an animal including mammals such as mice, by injecting a recombinant viral vector containing a specific gene for transfection at a region of the brain where a nerve terminal (a synapse terminal) is present, and by allowing the viral vector to be retrogradely transported through an axon, the target gene (a transgene) can be efficiently introduced for expression into a region of cell bodes in the central nervous system distant from the infected (injected) site of the viral vector. In particular, by using a kit for preparing a viral vector which utilizes a specific packaging plasmid, transfer plasmid and envelope gene, a viral vector having an unexpectedly higher virus titer can be obtained, and a recombinant viral vector showing a highly-frequent retrograde transportation ability in the brain can be advantageously produced.

DESCRIPTION OF EMBODIMENTS

Figure 1:
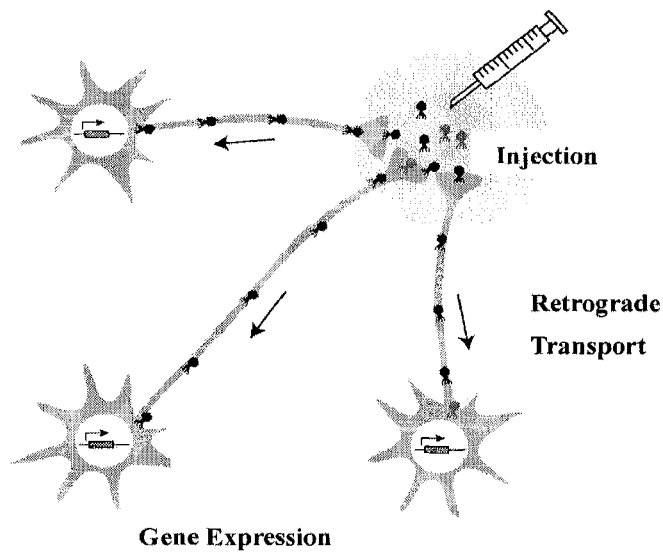
FIG. 1 shows a schematic overview of a HIV-1-pseudotype vector exhibiting highly-frequent retrograde transportation.

Now, embodiments of the present invention will be described. In the kit for preparing a viral vector according to the present invention, "gag" is a gene which encodes retroviral core proteins, and "pol" is a gene which encodes reverse transcriptase and the like. In addition, an "envelope gene" is a gene which encodes an envelope, a virus specific protein which is located in an envelope that is an outer membrane of a retrovirus comprised of a lipid bilayer membrane. The envelope plays an important role for a virus to adhere to and invade into a cell. Further, an "accessories gene" means, for example, the rev gene which regulates the expression of structural genes.

A preferred and representative example of the kit for preparing a viral vector according to the present invention is characterized by the use of "pCAGkGP1.1R" and "pCAG4-RTR2" as (1) a packaging plasmid containing the gag and the pol gene of HIV-1 and (2) a packaging plasmid containing an accessories gene of HIV-1 respectively, and further by the use of "pCL20 c-MSCV-X as a transfer plasmid where "X" represents a target gene. The target gene "X" to be transfected is encoded downstream of a mouse stem cell virus promoter in the above transfer plasmid.

Each plasmid contained in the above kit for preparing a viral vector is constructed based on a HIV-1 vector system "SJ1" developed by Dr. Arthur Nienhuis at St. Jude Children's Research Hospital (HANAWA, H., et al., (2002) Mol. Ther. 5, 242-251; (2004). Blood 103, 4062-4069. Supplied by St. Jude Children's Research Hospital). This vector system is known to show an about 10-fold greater titer in HeLa cells than other vector systems. Therefore, persons skilled in the art can readily produce each of these plasmids by referring to the specification of the present application and the above references. Note that the above (1) and (2) of the packaging plasmids may be constructed as one plasmid.

The envelope gene contained in the envelope plasmid of the kit for preparing a viral vector according to the present invention encodes a fused polypeptide comprising an extracellular domain of rabies virus glycoprotein (RV-G), a transmembrane domain of rabies virus glycoprotein (RV-G) or vesicular stomatitis virus glycoprotein (VSV-G) and an intracellular domain of vesicular stomatitis virus glycoprotein (VSV-G). Note that at the fusion boundaries of each domain, one or more amino acids can be optionally altered by deletion, insertion, substitution, or the like, and all of the amino acids constituting each domain are not necessarily included. Examples of the envelope gene can include an envelope gene encoding a fused polypeptide comprising the amino acid sequence shown in SEQ ID NO 2 (FuG-B), and preferably a nucleic acid molecule having the base sequence shown in SEQ ID NO 1 where the 1,440 bases (including start codon) at the 5' side are originated from RV-G and the 87 bases at the 3' side are originated from VSV-G Further, other examples of the envelope gene can include an envelope gene encoding a fused polypeptide comprised of the amino acid sequence shown in SEQ ID NO 6 (FuG-A), and preferably a nucleic acid molecule having the base sequence shown in SEQ ID NO 5 where the 1374 bases (including start codon) at the 5' side are originated from RV-G and the 147 bases at the 3' side are originated from VSV-G Given the codon degeneracy, the above base sequences can be optionally altered to optimize the codon along with other elements in the envelope plasmid. SEQ ID NOs 4 and 3 show examples of the amino acid sequence of rabies virus glycoprotein (RV-G) and the base sequence encoding thereof.

Thus, the above fused polypeptide is effective as an envelope to pseudotype various kinds of lentiviral vectors, in particular a HIV-1 lentiviral vector. Therefore, the present invention also relates to an envelope for pseudotyping a lentiviral vector comprised of the above fused polypeptide, a gene encoding an envelope comprising the above fused polypeptide, and an envelope plasmid itself containing the above gene.

In each of the plasmids contained in the kit for preparing a viral vector according to the present invention, each gene is linked under expression control of any expression regulatory sequences known to persons skilled in the art.

The phrase "under expression control of" means DNA encoding a given amino acid sequence has the ability to express a protein having that amino acid sequence under given conditions. In case that DNA encoding a given amino acid sequence is linked under expression control of an expression regulatory sequence, that DNA will express a given protein under given conditions. The term "an expression regulatory sequence" herein means a nucleic acid sequence that regulates expression of other nucleic acid sequences, and it regulates and modulates transcription and preferably even translation of other nucleic acid sequences. Expression regulatory sequences include an appropriate promoter, an enhancer, a transcription terminator, the start codon (namely, ATG) in a gene encoding a protein, a splicing signal for intron, a polyadenylation site and the stop codons.

The term "a promoter" means an essential sequence for transcription. Promoters also include promoter elements that regulate gene expression cell-type specifically, tissue specifically, or promoter-dependently via a signal or a modulator from the outside. A promoter element is linked at either the 5' or 3' region of DNA to be expressed. In addition, promoters include any of those constitutive or inducible. Promoters known for persons skilled in the art can be selected accordingly, depending on the classes of target genes and viral vectors to be used, the kinds of animals and brain diseases to be treated, pathological conditions of patients, and so on.

For example, in the envelope plasmid according to the present invention, an envelope gene is preferably linked such that it will be expressed under control of the cytomegalovirus enhancer and the avian β actin promoter. Such an envelope plasmid can be obtained by replacing, in accordance with the standard method, the base sequence encoding an extracellular domain and a transmembrane domain of vesicular stomatitis virus glycoprotein (VSV-G) with the base sequence encoding an extracellular domain and a transmembrane domain in the nucleic acid (cDNA) encoding a glycoprotein from a CVS strain of rabies virus (RV-G) which is passed in the brain of an infected infant mouse (provided by Dr. Kinjiro Morimoto at National Institute of Infectious Diseases) (Morimoto, K. et al., (1998) Proc Natl. Acad. Sci., USA 95, 3152-3156: SEQ ID NO 3) in the envelope plasmid "pCAGGS-VSV-G" included in the above vector system "SJ1". Therefore, persons skilled in the art can readily produce these plasmids described above by referring to the specification of the present application and the above references. Note that the glycoprotein (RV-G) of the rabies virus CVS strain is not limited to those having the base sequence shown in SEQ ID NO 3 above, but glycoproteins (RV-G) from any strains of any known rabies viruses can be used.

A target gene contained in a transfer plasmid known for persons skilled in the art can selected accordingly, depending on the intended use of a viral vector, the kinds of animals and brain diseases to be treated, pathological conditions of patients, and so on. Therefore, they include various genes of mammal, such as mouse, monkey and human, for example, a gene required for survival or protection of nigrostriatal system, which is used to treat cranial nerve diseases or neurodegenerative diseases represented by Parkinson's disease, etc. (for example, tyrosine hydroxylase, a neurotrophic factor from an glial cell line), or genes such as the interleukin-2 receptor α subunit (a target molecule of a recombinant immunotoxin) for research on cranial nerve systems and a light dependent ion channel, etc.

Host cells contained in the kit for producing a producer cell according to the present invention have no particular limitation as long as they can be infected by the above kit for preparing a viral vector so that they can produce a cell called "a producer cell" which can produce a retroviral particle. Any cells known to persons skilled in the art, for example, commercially available appropriate animal cells such as HEK293 T-cells (SV40 large T antigen is introduced) can be used.

Depending on their composition, intended use, etc., in addition to each of the above plasmids and/or host cells, the various kits according to the present invention can optionally contain other elements or ingredients known to persons skilled in the art, such as various reagents, buffers, various adjuvants, reaction plates (containers) and the like.

Using the kit for preparing a producer cell according to the present invention, a producer cell can be produced by co-transfecting an infected cell with a packaging plasmid, a transfer plasmid and an envelope plasmid contained in the kit for preparing a viral vector. This transfection is transient and can be performed by any methods known to persons skilled in the art, such as the calcium phosphate method.

A viral vector having a retrograde transport ability and a high titer in the brain can be produced by culturing the resultant producer cells using any methods or means known to persons skilled in the art, and harvesting virus particles from the culture supernatant.

A nerve terminal can be infected with the viral vector according to the invention, and the retrograde transportation of the viral vector through an axon of that nerve can introduce the viral vector into a cell body of that nerve at the target region in the brain, and a target gene can be expressed in the cell body. Target regions in the brain include primary motor cortex, primary somatosensory cortex, parafascicular nucleus of thalamus and substantia nigra pars compacta, which are projecting to striatum, and the brain center such as piriform cortex, subiculum, amygdala basolateral nucleus, anterior paraventricular nucleus, mediodorsal nucleus of thalamus and lateral hypothalamus, which are projecting to ventral striatum (nucleus accumbens). and a target gene can be expressed in the cell body. Further, the viral vector according to the present invention is retrogradely transported through an axon of motor neuron in the spinal cord.

Therefore, the viral vector according to the present invention is effective as an active ingredient of an agent for gene therapy. The agent for gene therapy can contain, in combination with the active ingredient, any pharmaceutically acceptable careers or diluents or other components known to persons skilled in the art.

The effective amount of the active ingredient according to the present invention can be selected accordingly by persons skilled in the art, depending on the classes of the transgene contained in the viral vector; the kinds and seriousness of brain diseases or neurodegenerative disorders; therapeutic strategy; age, body weight, sex, general health of patient; and racial (genetic) background of patient. A dose of the active ingredient (the viral vector) can be, for example, a total amount of $10^8$ to $10^9$ TU (Transducing Unit) per administration for several infection (injection) sites. Note that the viral vector or the agent for gene therapy can be infected (injected) at a predetermined site in a patient using any administration methods or devices known to persons skilled in the art.

By administering the viral vector according to the present invention to a patient, a gene introduced into a predetermined cell in a target region will be integrated into the chromosome of that cell, and the target gene will be stably expressed. Therefore, the present method of gene transfer can be used to perform gene therapy for brain diseases, neurodegenerative diseases (for example, Parkinson's disease) or the like of mammals including primate such as human.

Now, the present invention will be described in detail by Examples and test examples. These examples represent a part of the present invention, and the technical scope of the present invention is not limited at all by these Examples. Unless otherwise stated, experimental conditions and the like in each procedure were according to the methods described in the references cited herein, or the standard methods in the art.

EXAMPLES

Preparing a Viral Vector

Figure 2:
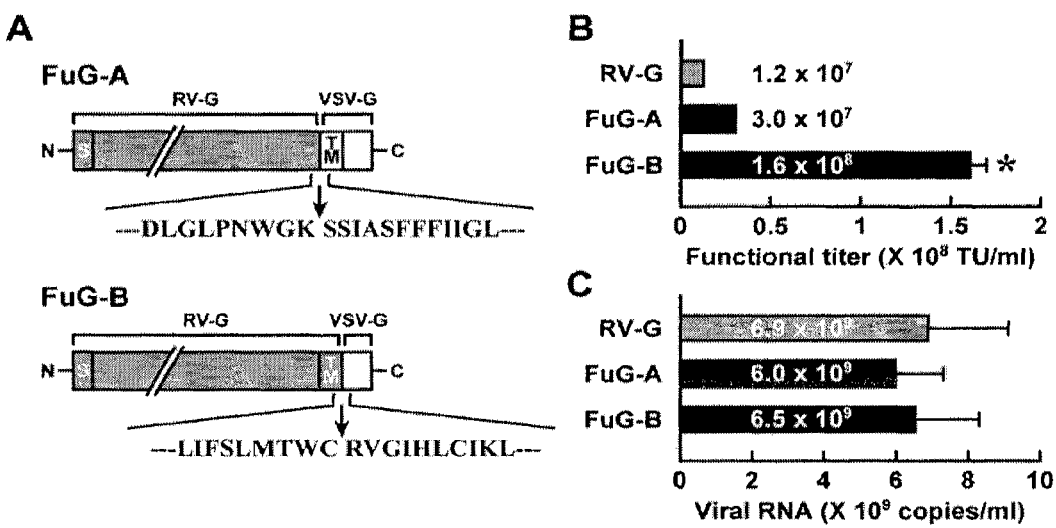
FIG. 2 shows the structures of other fused polypeptides according to the present invention and vector titers thereof. (A) The structure of FuG-A and FuG-B. FuG-A is comprised of an extracellular domain of RV-G, and a transmembrane domain and an intracellular domain of VSV-G. On the other hand, FuG-B is comprised of an extracellular domain and a transmembrane domain of RV-G, and an intracellular domain of VSV-G. S represents a signal peptide; TM represents a transmembrane domain. (B) Functional titers measured by FACS. (C) RNA titers measured by the reverse transcription-PCR method after extracting RNA from virus solutions. The values represent mean values from four experiments. *$P<0.001$ (Student t-test).

A viral vector according to the present invention was prepared using a HIV-1 vector system developed by Dr. Arthur Nienhuis at St. Jude Children's Research Hospital. Namely, a packaging plasmid containing the gag and pol gene (pCAGkGP1.1R), a packaging plasmid containing an accessories gene (pCAG4-RTR2) and a transfer plasmid containing a green fluorescence protein (GFP) as a target gene (pCL20 c-MSCV-GFP) were used. As an envelope plasmid, a vector containing a base sequence (SEQ ID NO 1) encoding an envelope was produced according to the conventional method, wherein the envelope is a fused polypeptide (FuG-B) in which an intracellular domain from VSV-G was linked to an extracellular domain and a transmembrane domain of the RV-G gene, which was provided by Dr. Kinjiro Morimoto at National Institute of Infectious Diseases (FIG. 2A, lower panel). Similarly, a vector containing a base sequence (SEQ ID NO 1) encoding an envelope was produced, wherein the envelope is a fused polypeptide (FuG-A) in which an extracellular domain from the RV-G gene was linked to a transmembrane domain and an intracellular domain from VSV-G (FIG. 2A, upper panel).

HEK293 T-cells (eighteen 10-cm dish) were transfected with a viral vector solution containing these plasmids using the calcium phosphate method. After cultured for 48 hours, virus particles were harvested from the culture supernatant and centrifuged, which was filtered with a 0.45-μm cellulose filter. Then, the vector particles were collected by centrifugation (10,000×g, 16 to 18 hours), and suspended in PBS. The suspension was subjected to Sepharose Q FF ion exchange column chromatography, which was washed with PBS and then eluted using a linear gradient from 0 to 1.5 M NaCl. Fractionations were monitored by the absorbance at 260/280 nm. Fractionations containing the vector particles were collected, concentrated using an ultrafiltration filter, and stored at −80° C.

In order to evaluate a virus titer, HEK293 T-cells were plated to a 6-well cell culture plate (MULTIWELL (R), FALCON) to infect the cultured cells with an appropriate concentration of the virus solution. Titers were measured using FACS Calibur (Nippon Becton Dickinson Co., Tokyo, Japan) (FIG. 2B). In addition, in order to compare production efficiency of the vectors, the amount of RNA contained in the viral genome was measured using the reverse transcription-PCR method. No significant change in the RNA titers was observed between the both vectors (FIG. 2C). In order to compare transfection efficiency into cells, values were calculated by dividing a functional titer by an RNA titer. The results showed that the RV-G vector had a value of $1.7 \times 10^{-3}$, the FuG-A vector had a value of $5.0 \times 10^{-3}$, and the FuG-B vector had a value of $2.5 \times 10^{-2}$. As compared with the transfection efficiency of the RV-G vector, the transfection efficiency of the FuG-A vector and the FuG-B vector was shown to be increased by about 2.9 times and about 15 times respectively. These results clearly showed that the use of FuG-B as an envelope can significantly improve a functional titer without affecting the production efficiency of the vector.

Example 2

Introducing a Viral Vector into a Mouse Brain

Animal care and use was performed according to a guideline by the animal care and use committee of Fukushima Medical University.

Figure 3:
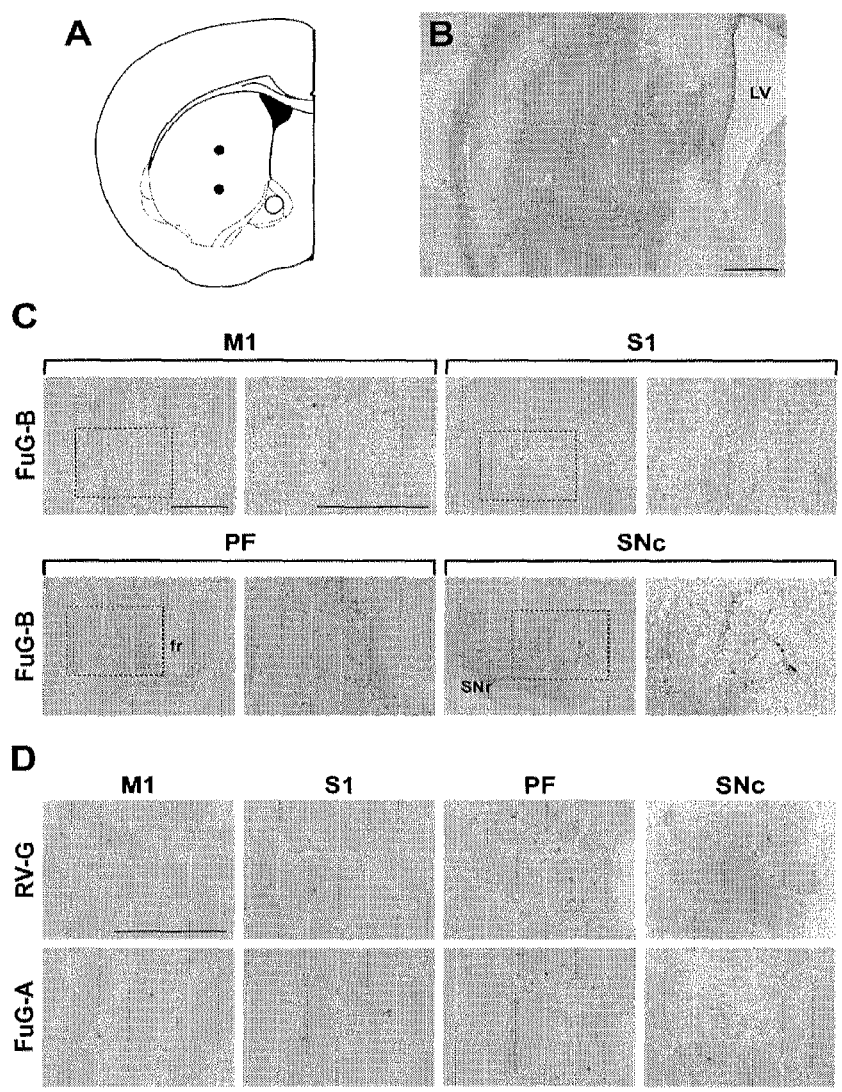
FIG. 3 shows the expression of the transgene at regions in the brain projecting to striatum. (A) The coordinates of the injected site. (B) The expression of the transgene at striatum. (C) The expression of the transgene via retrograde transportation in an animal which was injected with the FuG-B vector ($1.2\times10^{10}$ copies/ml) at striatum. Many immunopositive cells were observed in primary motor cortex (M1), primary somatosensory cortex (S1), parafascicular nucleus of thalamus (PF), substantia nigra pars compacta (SNc). (D) The expression of the transgene via retrograde transportation in an animal which was injected with the RV-G vector and the FuG-A vector (having a similar RNA titer as above) within striatum. Only enlarged images are shown. Scale bar: 500 µm.

A 12-week old mouse (C57BL/6J) was anesthetized with pentobarbital sodium (50 mg/kg, i.p.), and a solution containing a vector produced as described above ($1.2 \times 10^{10}$ copies/ml) was injected in the brain (striatum) of the mouse using a brain stereotaxic apparatus. The injection was performed according to the mouse brain atlas (PAXINOS, G, and FRANKLIN, K. B. J. (2001). The Mouse Brain in Stereotaxic Coordinates, 2nd edn. (Academic Press, San Diego). FIG. 3A shows that 2 μl of the solution was injected (0.1 μl/min) at two points along the track respectively in the dorsal region of striatum through a glass microinjection capillary connected to a microinjection pump. Anteroposterior, mediolateral and dorsoventral coordinates from bregma were 0.50, 2.00 and 2.50/3.25 (mm), respectively.

Three weeks after the injection, a mouse was deeply anesthetized with pentobarbital sodium (50 mg/kg, i.p.), and then the brain was perfused and fixed with 4% formalin and 0.1 M phosphate buffer (PB: pH 7.4) via the heart before extirpating the brain. Sections were prepared using a cryostat and analyzed using the immunostaining method. The FuG-B vector induced the expression of the transgene in many cells in striatum (FIG. 3B). In addition, the expression of the transgene was analyzed by the immunostaining method in primary motor cortex, primary somatosensory cortex, parafascicular nucleus of thalamus and substantia nigra pars compacta, which are representative brain regions projecting to striatum. The results showed that many nerve cells expressing the transgene were observed in these regions (FIG. 3C). In order to compare the transfection efficiencies of the RV-G and FuG-A vectors, these vectors having the same RNA titer ($1.2 \times 10^{10}$ copies/ml) were injected in a similarly fashion, and a pattern of retrograde gene transfer was analyzed (FIG. 3D). Only a few positive cells were found in primary motor cortex, primary somatosensory cortex, parafascicular nucleus of thalamus and substantia nigra pars compacta. The number of cells in each section was counted and the numbers of positive cells were compared among the three vectors (Table 1). The number of cells per section is shown as a mean value±standard error (n=4). *$P<0.001$ vs. RV-G (ANOVA/Tukey HSD).

TABLE 1

| | Brain region | | | |
|---|---|---|---|---|
| | M1 | S1 | PF | SNc |
| RV-G | 7.5 ± 0.7 | 7.4 ± 0.3 | 17.5 ± 1.8 | 0.4 ± 0.1 |
| FuG-A | 9.3 ± 0.2 | 10.5 ± 0.6 | 21.9 ± 1.0 | 0.5 ± 0.1 |
| FuG-B | 87.2 ± 4.1* | 87.7 ± 2.9* | 134.8 ± 5.7* | 5.5 ± 0.8* |

As seen from the results shown in Table 1, the FuG-B vector clearly showed an increased number of positive cells in all of the four brain regions as compared with the RV-G vector. Fold increases for the FuG-B vector were 12 fold, 12 fold, 8 fold and 14 fold for primary motor cortex, primary somatosensory cortex, parafascicular nucleus of thalamus and substantia nigra pars compacta, respectively. On the other hand, the FuG-A vector showed a tendency of increased positive cells compared with the RV-G vector. From these results, pseudotyping using FuG-B was found to significantly increase the transfection efficiency of gene transfer through retrograde transportation.

Example 3

Figure 4:
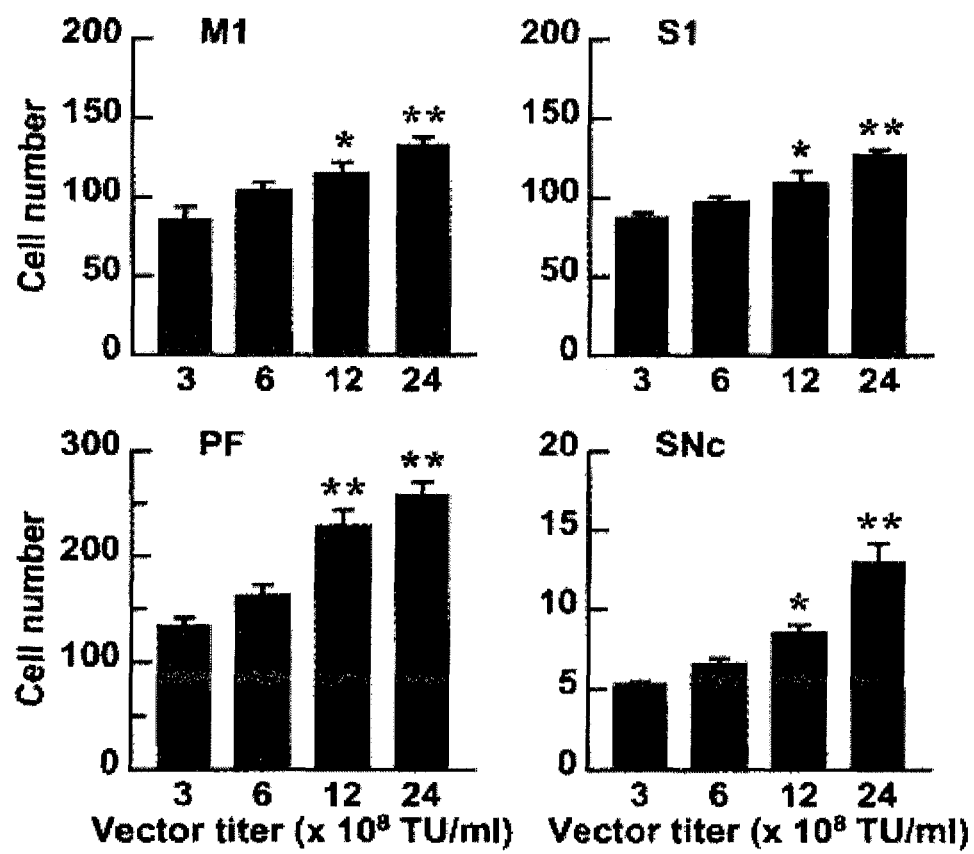
FIG. 4 shows changes in the expression levels of the retrograde gene correlated with vector titers. The FuG-B vectors with various titers ($3.0\times10^{8}$ to $2.4\times10^{9}$ TU/ml) was injected into striatum to immunostain sections of primary motor cortex (M1), primary somatosensory cortex (S1), parafascicular nucleus of thalamus (PF), substantia nigra pars compacta (SNc) using anti-GFP antibody. Cells expressing the transgene at each brain region were counted. Several sections were prepared from each animal, and positive cells in each brain region were counted to calculate mean values. The value in the figure shows the mean±standard error of the values obtained from four animals. ANOVA, *$P<0.05$, **$P<0.01$ (Tukey-HSD test).

In order to analyze the effects of vector titers on the efficiency of retrograde gene transfer, the FuG-B vectors having various titers ($3.0 \times 10^8$ to $2.4 \times 10^9$ TU/ml) were injected into striatum in a similar manner as in Example 2. The expression of the transgene was then analyzed by the immunostaining method using anti-GFP antibody in primary motor cortex (M1), primary somatosensory cortex (S1), parafascicular nucleus of thalamus (PF) and substantia nigra pars compacta (SNc). Positive cells in each of the brain regions were counted (FIG. 4). The results showed that, in the four brain regions, the number of positive cells was significantly increased as the vector titer was increased. These results showed that the efficiency of retrograde gene transfer was dependent on the vector titer.

Example 4

Figure 5:
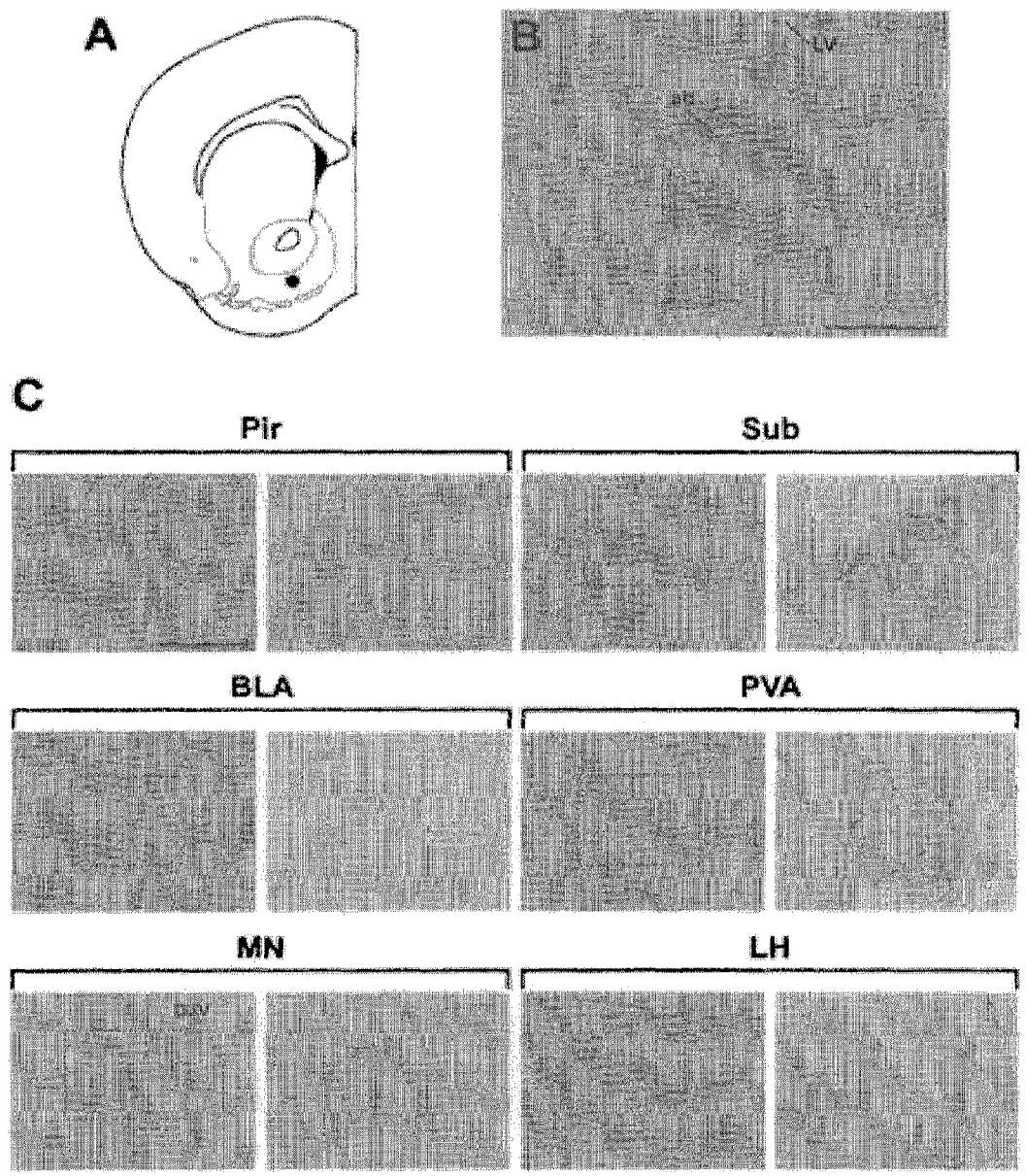
FIG. 5 shows the expression of the transgene at regions in the brain projecting to nucleus accumbens. Brain sections were prepared from an animal which was injected with the FuG-B vector ($3\times10^{8}$ TU/ml) within the nucleus accumbens to immunostain them with anti-GFP antibody. (A) The coordinates of the injected site. (B) The expression of the transgene at the nucleus accumbens. (C) The expression of the transgene via retrograde transportation. Immunopositive cells were observed at Piriform cortex (Pir), Subiculum (Sub), Amygdala basolateral nucleus (BLA), anterior paraventricular nucleus (PVA), mediodorsal nucleus of thalamus (MN), lateral hypothalamus (LH). ac (anterior commissure), D3V (third ventricle), LV (lateral ventricle). Scale bar: 500 µm.

In order to analyze a pattern of gene expression in other brain regions, the FuG-B vector ($3 \times 10^8$ TU/ml) was injected into ventral striatum (nucleus accumbens) (FIG. 5A). The FuG-B vector induced the expression of the transgene in many cells in nucleus accumbens (FIG. 5B). In addition, immunopositive cells were observed and the expression of the transgene was detected in piriform cortex (Pir), subiculum (Sub), amygdala basis lateral nucleus (BLA), anterior paraventricular nucleus (PVA), mediodorsal nucleus of thalamus (MN), lateral hypothalamus (LH), which project to nucleus accumbens (FIG. 5C). The above results showed that the FuG-B vector was capable of highly-frequent retrograde transportation at various regions in the brain.

Figure 6:
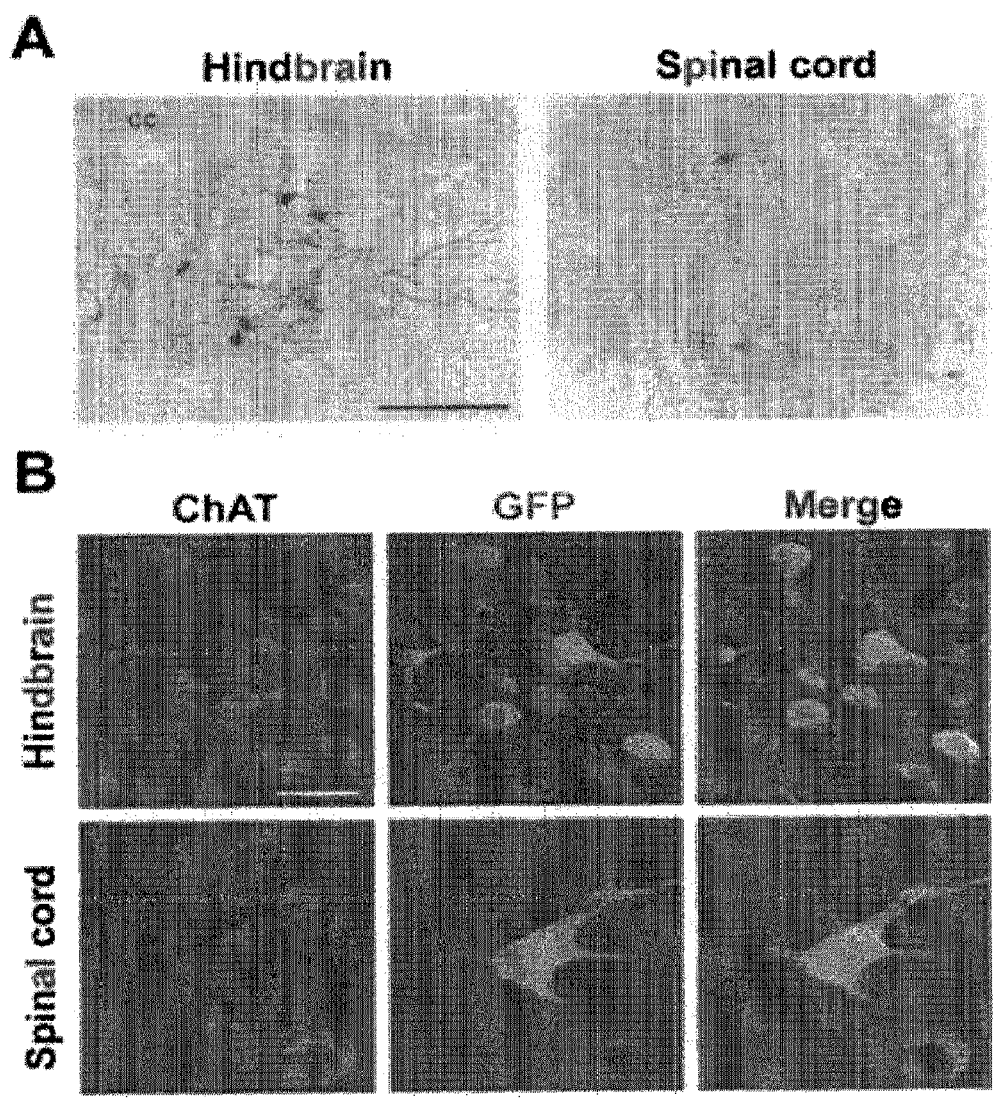
FIG. 6 shows the result from gene transfer into motoneuron by intramuscular injection. Sections of the metencephalon and the spinal cord (lumbar region) were prepared from an animal which was intramuscularly injected with the FuG-B vector ($2.4\times10^{9}$ TU/ml) at the ingual muscles or the hindlimb to immunostain them with anti-GFP antibody. (A) The expression of the transgene at the metencephalon hypoglossal nucleus and the ventral side of the spinal cord. (B) Doublestaining of the sections. The expression of GFP (green) overlaps with the expression of ChAT (red). Scale bar: 200 µm (A), 50 µm (B).

Further, a possibility of gene transfer into a motor neuron in the metencephalon and the spinal cord via intramuscular injection was examined. After injecting the FuG-B vector ($2.4 \times 10^9$ TU/ml) into lingual muscle or hindlimb muscle, the expression of the transgene was observed in hypoglossal nucleus in the metencephalon (hindbrain) and the ventral side of the spinal cord (lumbar region) (FIG. 6A). The results from double staining with the antibody against choline acetyltransferase (ChAT), a marker for motor neurons, and anti-GFP antibody indicated that positive cells in the ventral side of the spinal cord were motor neurons (FIG. 6B). These results showed the efficient retrograde transportation of the FuG-B vector at various regions in the central nervous system.

Histological Procedures

For immunostaining by the avidin-biotin-peroxidase method, transverse sections (for mice: thickness of 30 μm) were prepared using a cryostat. The sections were then incubated with rabbit anti-GFP polyclonal antibody (Molecular Probes, Eugene, Oreg.: 1:2,000 dilution), and further incubated with a biotinylated goat anti-rabbit IgG antibody (Vector Laboratories, Burlingame, Calif.: 1:1,000 dilution). Immunoreaction signals were visualized by the Vectastain Elite ABC kit (Vector Laboratories, Burlingame, Calif.).

For double immunofluorescence histochemical staining, the sections were incubated with either one of the above rabbit anti-GFP polyclonal antibody or anti-choline acetyltransferase mouse antibody (Chemicon, Temecula, Calif.: 1:100 dilution). Then, the sections were incubated with FITC-conjugated goat anti-rabbit IgG and Cy3-conjugated donkey anti-mouse antibody (1:500 dilution, Jackson, ImmunoResearch Laboratories, West Groove, Pa.). Fluorescence images were captured under a confocal laser scanning microscope (LSM510, Zeiss, Thornwood, N.Y.) equipped with a filter cube having a suitable specification for FITC and Cy3 fluorescence channels. These fluorescence images were taken with an advanced CCD camera system controlled by the Zeiss Axiovision software package.

Cell Count

Immunostaining by the above avidin-biotin-peroxidase method was performed using a series of sections passing through the forebrain and the midbrain. The number of immunostained cells in each brain region was counted by a computer-controlled graphics program (NIH Image 1.62, National Institutes of Health, Bethesda, Md.). In order to identify striatum cells at the injection site of the vector, double immunofluorescence histochemical staining was performed using representative sections. In each animal, the number of immunostained cells within the target region was counted by the graphics program. Using 8 to 10 sections from each animal, a mean value per section was calculated.

Contents described in the references cited herein constitute the contents of the disclosure of the present specification as a part of the present specification.

INDUSTRIAL APPLICABILITY

The present invention allows high yield production of a lentiviral vector which shows highly-frequent retrograde transportation in the brain of an animal. This lentiviral vector allows retrograde transportation of the vector and introduction of a target gene into a region of cell bodies by injecting the vector into a region in the brain where a nerve terminal presents. Therefore, the present invention provides an effective technology for gene therapy of cranial nerve diseases such as Parkinson's disease.

In addition, the present invention is to provide a novel and effective technology for experiments for gene therapy of cranial nerve diseases and for creating a disease model.

What is claimed is:

1. A kit for preparing a retrograde transport viral vector comprising:

(A) a first packaging plasmid containing the gag gene and the pol gene of HIV-1;

(B) a second packaging plasmid containing an accessory gene of HIV-1;

(C) a transfer plasmid containing a target gene; and (D) an envelope plasmid containing an envelope gene encoding a chimeric envelope protein, wherein the chimeric envelope protein comprises the amino acid sequence of SEQ ID NO: 2.

2. The kit for preparing a viral vector according to claim 1, wherein the envelope gene is expressed under control of a cytomegalovirus enhancer and an avian β-actin promoter in the envelope plasmid.

3. The kit for preparing a viral vector according to claim 2, wherein the envelope gene comprises SEQ ID NO 1.

4. A kit for producing a producer cell, comprising the kit for preparing a viral vector according to claim 1 and a host cell.

5. The kit according to claim 4, wherein the host cell is a HEK293 T-cell.

6. A method of producing a producer cell, comprising:

co-transfecting a host cell with the first and the second packaging plasmids, the transfer plasmid, and the envelope plasmid contained in the kit of claim 1.

7. The method according to claim 6, wherein the host cell is a HEK293 T-cell.

8. The method according to claim 6, wherein the transfection is performed using a calcium phosphate method.

9. A producer cell obtained by the method according to claim 6.

10. A method of producing a viral vector, comprising:

culturing the producer cell according to claim 9 to form a cell culture with supernatant; and harvesting a virus particle from the supernatant of the culture.

11. A viral vector possessing a retrograde transportation ability, produced by the method according to claim 10.

12. A chimeric envelope comprising a fused polypeptide, wherein the fused polypeptide comprises the amino acid sequence of SEQ ID NO: 2, and wherein the chimeric envelope is capable of pseudotyping an HIV-1 lentivirus vector system to produce pseudotyped particles comprising said chimeric envelope such that the pseudotyped virus particles can facilitate retrograde gene transfer into neurons.

13. An isolated nucleic acid encoding the chimeric envelope according to claim 12.

14. An envelope plasmid comprising the nucleic acid according to claim 13.

15. A pseudotyped retrovirus particle comprising the chimeric envelope according to claim 12.

* * * * *

SEQUENCE LISTING

<160> NUMBER OF SEQ ID NOS: 6

<210> SEQ ID NO 1
<211> LENGTH: 1530
<212> TYPE: DNA
<213> ORGANISM: Artificial Sequence
<220> FEATURE:
<223> OTHER INFORMATION: Fused Polypeptide (FuG-B)
<220> FEATURE:
<221> NAME/KEY: CDS
<222> LOCATION: (1)..(1530)

<400> SEQUENCE: 1

```
atg gtt ccg cag gtt ctt ttg ttt gta ctc ctt ctg ggt ttt tcg ttg      48
Met Val Pro Gln Val Leu Leu Phe Val Leu Leu Leu Gly Phe Ser Leu
 1               5                  10                  15 tgt ttc ggg aag ttc ccc att tac acg ata cca gac gaa ctt ggt ccc      96
Cys Phe Gly Lys Phe Pro Ile Tyr Thr Ile Pro Asp Glu Leu Gly Pro
             20                  25                  30 tgg agc cct att gac ata cac cat ctc agc tgt cca aat aac ctg gtt     144
Trp Ser Pro Ile Asp Ile His His Leu Ser Cys Pro Asn Asn Leu Val
         35                  40                  45 gtg gag gat gaa gga tgt acc aac ctg tcc gag ttc tcc tac atg gaa     192
Val Glu Asp Glu Gly Cys Thr Asn Leu Ser Glu Phe Ser Tyr Met Glu
     50                  55                  60 ctc aaa gtg gga tac atc tca gcc atc aaa gtg aac ggg ttc act tgc     240
Leu Lys Val Gly Tyr Ile Ser Ala Ile Lys Val Asn Gly Phe Thr Cys
 65                  70                  75                  80 aca ggt gtt gtg aca gag gca gag acc tac acc aac ttt gtt ggt tat     288
Thr Gly Val Val Thr Glu Ala Glu Thr Tyr Thr Asn Phe Val Gly Tyr
                 85                  90                  95 gtc aca acc aca ttc aag aga aag cat ttc cgc ccc acc cca gac gca     336
Val Thr Thr Thr Phe Lys Arg Lys His Phe Arg Pro Thr Pro Asp Ala
            100                 105                 110 tgt aga gcc gcg tat aac tgg aag atg gcc ggt gac ccc aga tat gaa     384
Cys Arg Ala Ala Tyr Asn Trp Lys Met Ala Gly Asp Pro Arg Tyr Glu
        115                 120                 125 gag tcc cta cac aat cca tac ccc gac tac cac tgg ctt cga act gta     432
Glu Ser Leu His Asn Pro Tyr Pro Asp Tyr His Trp Leu Arg Thr Val
    130                 135                 140 aga acc acc aaa gag tcc ctc att atc ata tcc cca agt gtg aca gat     480
Arg Thr Thr Lys Glu Ser Leu Ile Ile Ile Ser Pro Ser Val Thr Asp
145                 150                 155                 160 ttg gac cca tat gac aaa tcc ctt cac tca agg gtc ttc cct ggc gga     528
Leu Asp Pro Tyr Asp Lys Ser Leu His Ser Arg Val Phe Pro Gly Gly
                165                 170                 175 aag tgc tca gga ata acg gtg tcc tct acc tac tgc tca act aac cat     576
Lys Cys Ser Gly Ile Thr Val Ser Ser Thr Tyr Cys Ser Thr Asn His
            180                 185                 190 gat tac acc att tgg atg ccc gag aat ccg aga cca agg aca cct tgt     624
Asp Tyr Thr Ile Trp Met Pro Glu Asn Pro Arg Pro Arg Thr Pro Cys
        195                 200                 205 gac att ttt acc aat agc aga ggg aag aga gca tcc aac ggg aac aag     672
Asp Ile Phe Thr Asn Ser Arg Gly Lys Arg Ala Ser Asn Gly Asn Lys
    210                 215                 220 act tgc ggc ttt gtg gat gaa aga ggc ctg tat aag tct cta aaa gga     720
Thr Cys Gly Phe Val Asp Glu Arg Gly Leu Tyr Lys Ser Leu Lys Gly
225                 230                 235                 240 gca tgc agg ctc aag tta tgt gga gtt ctt gga ctt aga ctt atg gat     768
Ala Cys Arg Leu Lys Leu Cys Gly Val Leu Gly Leu Arg Leu Met Asp
                245                 250                 255
```

```
gga aca tgg gtc gcg atg caa aca tca gat gag acc aaa tgg tgc cct    816
Gly Thr Trp Val Ala Met Gln Thr Ser Asp Glu Thr Lys Trp Cys Pro
            260                 265                 270 cca gat cag ttg gtg aat ttg cac gac ttt cgc tca gac gag atc gag    864
Pro Asp Gln Leu Val Asn Leu His Asp Phe Arg Ser Asp Glu Ile Glu
        275                 280                 285 cat ctc gtt gtg gag gag tta gtt aag aaa aga gag gaa tgt ctg gat    912
His Leu Val Val Glu Glu Leu Val Lys Lys Arg Glu Glu Cys Leu Asp
    290                 295                 300 gca tta gag tcc atc atg acc acc aag tca gta agt ttc aga cgt ctc    960
Ala Leu Glu Ser Ile Met Thr Thr Lys Ser Val Ser Phe Arg Arg Leu
305                 310                 315                 320 agt cac ctg aga aaa ctt gtc cca ggg ttt gga aaa gca tat acc ata   1008
Ser His Leu Arg Lys Leu Val Pro Gly Phe Gly Lys Ala Tyr Thr Ile
            325                 330                 335 ttc aac aaa acc ttg atg gag gct gat gct cac tac aag tca gtc cgg   1056
Phe Asn Lys Thr Leu Met Glu Ala Asp Ala His Tyr Lys Ser Val Arg
        340                 345                 350 acc tgg aat gag atc atc ccc tca aaa ggg tgt ttg aaa gtt gga gga   1104
Thr Trp Asn Glu Ile Ile Pro Ser Lys Gly Cys Leu Lys Val Gly Gly
    355                 360                 365 agg tgc cat cct cat gtg aac ggg gtg ttt ttc aat ggt ata ata tta   1152
Arg Cys His Pro His Val Asn Gly Val Phe Phe Asn Gly Ile Ile Leu
370                 375                 380 ggg cct gac gac cat gtc cta atc cca gag atg caa tca tcc ctc ctc   1200
Gly Pro Asp Asp His Val Leu Ile Pro Glu Met Gln Ser Ser Leu Leu
385                 390                 395                 400 cag caa cat atg gag ttg ttg gaa tct tca gtt atc ccc ctg atg cac   1248
Gln Gln His Met Glu Leu Leu Glu Ser Ser Val Ile Pro Leu Met His
            405                 410                 415 ccc ctg gca gac cct tct aca gtt ttc aaa gaa ggt gat gag gct gag   1296
Pro Leu Ala Asp Pro Ser Thr Val Phe Lys Glu Gly Asp Glu Ala Glu
        420                 425                 430 gat ttt gtt gaa gtt cac ctc ccc gat gtg tac aaa cag atc tca ggg   1344
Asp Phe Val Glu Val His Leu Pro Asp Val Tyr Lys Gln Ile Ser Gly
    435                 440                 445 gtt gac ctg ggt ctc ccg aac tgg gga aag tat gta ttg atg act gca   1392
Val Asp Leu Gly Leu Pro Asn Trp Gly Lys Tyr Val Leu Met Thr Ala
450                 455                 460 ggg gcc atg att ggc ctg gtg ttg ata ttt tcc cta atg aca tgg tgc   1440
Gly Ala Met Ile Gly Leu Val Leu Ile Phe Ser Leu Met Thr Trp Cys
465                 470                 475                 480 aga gtt ggt atc cat ctt tgc att aaa tta aag cac acc aag aaa aga   1488
Arg Val Gly Ile His Leu Cys Ile Lys Leu Lys His Thr Lys Lys Arg
            485                 490                 495 cag att tat aca gac ata gag atg aac cga ctt gga aag taa           1530
Gln Ile Tyr Thr Asp Ile Glu Met Asn Arg Leu Gly Lys
        500                 505
```

<210> SEQ ID NO 2
<211> LENGTH: 509
<212> TYPE: PRT
<213> ORGANISM: Artificial Sequence
<220> FEATURE:
<223> OTHER INFORMATION: Fused Polypeptide (FuG-B)

<400> SEQUENCE: 2

```
Met Val Pro Gln Val Leu Leu Phe Val Leu Leu Leu Gly Phe Ser Leu
1               5                   10                  15

Cys Phe Gly Lys Phe Pro Ile Tyr Thr Ile Pro Asp Glu Leu Gly Pro
            20                  25                  30
```

-continued

Trp Ser Pro Ile Asp Ile His His Leu Ser Cys Pro Asn Asn Leu Val
    35                  40                  45

Val Glu Asp Glu Gly Cys Thr Asn Leu Ser Glu Phe Ser Tyr Met Glu
50                      55                  60

Leu Lys Val Gly Tyr Ile Ser Ala Ile Lys Val Asn Gly Phe Thr Cys
65                  70                  75                  80

Thr Gly Val Val Thr Glu Ala Glu Thr Tyr Thr Asn Phe Val Gly Tyr
                85                  90                  95

Val Thr Thr Thr Phe Lys Arg Lys His Phe Arg Pro Thr Pro Asp Ala
                100                 105                 110

Cys Arg Ala Ala Tyr Asn Trp Lys Met Ala Gly Asp Pro Arg Tyr Glu
            115                 120                 125

Glu Ser Leu His Asn Pro Tyr Pro Asp Tyr His Trp Leu Arg Thr Val
        130                 135                 140

Arg Thr Thr Lys Glu Ser Leu Ile Ile Ser Pro Ser Val Thr Asp
145                 150                 155                 160

Leu Asp Pro Tyr Asp Lys Ser Leu His Ser Arg Val Phe Pro Gly Gly
                165                 170                 175

Lys Cys Ser Gly Ile Thr Val Ser Ser Thr Tyr Cys Ser Thr Asn His
                180                 185                 190

Asp Tyr Thr Ile Trp Met Pro Glu Asn Pro Arg Pro Arg Thr Pro Cys
            195                 200                 205

Asp Ile Phe Thr Asn Ser Arg Gly Lys Arg Ala Ser Asn Gly Asn Lys
    210                 215                 220

Thr Cys Gly Phe Val Asp Glu Arg Gly Leu Tyr Lys Ser Leu Lys Gly
225                 230                 235                 240

Ala Cys Arg Leu Lys Leu Cys Gly Val Leu Gly Leu Arg Leu Met Asp
                245                 250                 255

Gly Thr Trp Val Ala Met Gln Thr Ser Asp Glu Thr Lys Trp Cys Pro
            260                 265                 270

Pro Asp Gln Leu Val Asn Leu His Asp Phe Arg Ser Asp Glu Ile Glu
    275                 280                 285

His Leu Val Val Glu Glu Leu Val Lys Lys Arg Glu Glu Cys Leu Asp
    290                 295                 300

Ala Leu Glu Ser Ile Met Thr Thr Lys Ser Val Ser Phe Arg Arg Leu
305                 310                 315                 320

Ser His Leu Arg Lys Leu Val Pro Gly Phe Gly Lys Ala Tyr Thr Ile
                325                 330                 335

Phe Asn Lys Thr Leu Met Glu Ala Asp Ala His Tyr Lys Ser Val Arg
                340                 345                 350

Thr Trp Asn Glu Ile Ile Pro Ser Lys Gly Cys Leu Lys Val Gly Gly
            355                 360                 365

Arg Cys His Pro His Val Asn Gly Val Phe Phe Asn Gly Ile Ile Leu
    370                 375                 380

Gly Pro Asp Asp His Val Leu Ile Pro Glu Met Gln Ser Ser Leu Leu
385                 390                 395                 400

Gln Gln His Met Glu Leu Leu Glu Ser Ser Val Ile Pro Leu Met His
                405                 410                 415

Pro Leu Ala Asp Pro Ser Thr Val Phe Lys Glu Gly Asp Glu Ala Glu
                420                 425                 430

Asp Phe Val Glu Val His Leu Pro Asp Val Tyr Lys Gln Ile Ser Gly
            435                 440                 445

```
Val Asp Leu Gly Leu Pro Asn Trp Gly Lys Tyr Val Leu Met Thr Ala
    450                 455                 460

Gly Ala Met Ile Gly Leu Val Leu Ile Phe Ser Leu Met Thr Trp Cys
465                 470                 475                 480

Arg Val Gly Ile His Leu Cys Ile Lys Leu Lys His Thr Lys Lys Arg
                485                 490                 495

Gln Ile Tyr Thr Asp Ile Glu Met Asn Arg Leu Gly Lys
            500                 505

<210> SEQ ID NO 3
<211> LENGTH: 1575
<212> TYPE: DNA
<213> ORGANISM: Rabies Virus
<220> FEATURE:
<221> NAME/KEY: CDS
<222> LOCATION: (1)..(1575)

<400

```
act tgc ggc ttt gtg gat gaa aga ggc ctg tat aag tct cta aaa gga      720
Thr Cys Gly Phe Val Asp Glu Arg Gly Leu Tyr Lys Ser Leu Lys Gly
225                 230                 235                 240 gca tgc agg ctc aag tta tgt gga gtt ctt gga ctt aga ctt atg gat      768
Ala Cys Arg Leu Lys Leu Cys Gly Val Leu Gly Leu Arg Leu Met Asp
                245                 250                 255 gga aca tgg gtc gcg atg caa aca tca gat gag acc aaa tgg tgc cct      816
Gly Thr Trp Val Ala Met Gln Thr Ser Asp Glu Thr Lys Trp Cys Pro
            260                 265                 270 cca gat cag ttg gtg aat ttg cac gac ttt cgc tca gac gag atc gag      864
Pro Asp Gln Leu Val Asn Leu His Asp Phe Arg Ser Asp Glu Ile Glu
        275                 280                 285 cat ctc gtt gtg gag gag tta gtc aag aaa aga gag gaa tgt ctg gat      912
His Leu Val Val Glu Glu Leu Val Lys Lys Arg Glu Glu Cys Leu Asp
    290                 295                 300 gca tta gag tcc atc atg acc acc aag tca gta agt ttc aga cgt ctc      960
Ala Leu Glu Ser Ile Met Thr Thr Lys Ser Val Ser Phe Arg Arg Leu
305                 310                 315                 320 agt cac ctg aga aaa ctt gtc cca ggg ttt gga aaa gca tat acc ata     1008
Ser His Leu Arg Lys Leu Val Pro Gly Phe Gly Lys Ala Tyr Thr Ile
                325                 330                 335 ttc aac aaa acc ttg atg gag gct gat gct cac tac aag tca gtc cgg     1056
Phe Asn Lys Thr Leu Met Glu Ala Asp Ala His Tyr Lys Ser Val Arg
            340                 345                 350 acc tgg aat gag atc atc ccc tca aaa ggg tgt ttg aaa gtt gga gga     1104
Thr Trp Asn Glu Ile Ile Pro Ser Lys Gly Cys Leu Lys Val Gly Gly
        355                 360                 365 agg tgc cat cct cat gtg aac ggg gtg ttt ttc aat ggt ata ata tta     1152
Arg Cys His Pro His Val Asn Gly Val Phe Phe Asn Gly Ile Ile Leu
    370                 375                 380 ggg cct gac gac cat gtc cta atc cca gag atg caa tca tcc ctc ctc     1200
Gly Pro Asp Asp His Val Leu Ile Pro Glu Met Gln Ser Ser Leu Leu
385                 390                 395                 400 cag caa cat atg gag ttg ttg gaa tct tca gtt atc ccc ctg atg cac     1248
Gln Gln His Met Glu Leu Leu Glu Ser Ser Val Ile Pro Leu Met His
                405                 410                 415 ccc ctg gca gac cct tct aca gtt ttc aaa gaa ggt gat gag gct gag     1296
Pro Leu Ala Asp Pro Ser Thr Val Phe Lys Glu Gly Asp Glu Ala Glu
            420                 425                 430 gat ttt gtt gaa gtt cac ctc ccc gat gtg tac aaa cag atc tca ggg     1344
Asp Phe Val Glu Val His Leu Pro Asp Val Tyr Lys Gln Ile Ser Gly
        435                 440                 445 gtt gac ctg ggt ctc ccg aac tgg gga aag tat gta ttg atg act gca     1392
Val Asp Leu Gly Leu Pro Asn Trp Gly Lys Tyr Val Leu Met Thr Ala
    450                 455                 460 ggg gcc atg att ggc ctg gtg ttg ata ttt tcc cta atg aca tgg tgc     1440
Gly Ala Met Ile Gly Leu Val Leu Ile Phe Ser Leu Met Thr Trp Cys
465                 470                 475                 480 aga aga gcc aat cga cca gaa tcg aaa caa cgc agt ttt gga ggg aca     1488
Arg Arg Ala Asn Arg Pro Glu Ser Lys Gln Arg Ser Phe Gly Gly Thr
                485                 490                 495 ggg ggg aat gtg tca gtc act tcc caa agc gga aaa gtc ata cct tca     1536
Gly Gly Asn Val Ser Val Thr Ser Gln Ser Gly Lys Val Ile Pro Ser
            500                 505                 510 tgg gaa tca tat aag agt gga ggt gag acc agg ctg tga                 1575
Trp Glu Ser Tyr Lys Ser Gly Gly Glu Thr Arg Leu
        515                 520

<210> SEQ ID NO 4
<211> LENGTH: 524
```

<212> TYPE: PRT
<213> ORGANISM: Rabies Virus

<400> SEQUENCE: 4

```
Met Val Pro Gln Val

```
Gln Gln His Met Glu Leu Leu Glu Ser Ser Val Ile Pro Leu Met His
            405                 410                 415
Pro Leu Ala Asp Pro Ser Thr Val Phe Lys Glu Gly Asp Glu Ala Glu
        420                 425                 430
Asp Phe Val Glu Val His Leu Pro Asp Val Tyr Lys Gln Ile Ser Gly
    435                 440                 445
Val Asp Leu Gly Leu Pro Asn Trp Gly Lys Tyr Val Leu Met Thr Ala
450                 455                 460
Gly Ala Met Ile Gly Leu Val Leu Ile Phe Ser Leu Met Thr Trp Cys
465                 470                 475                 480
Arg Arg Ala Asn Arg Pro Glu Ser Lys Gln Arg Ser Phe Gly Gly Thr
                485                 490                 495
Gly Gly Asn Val Ser Val Thr Ser Gln Ser Gly Lys Val Ile Pro Ser
            500                 505                 510
Trp Glu Ser Tyr Lys Ser Gly Gly Glu Thr Arg Leu
        515                 520

<210> SEQ ID NO 5
<211> LENGTH: 1524
<212> TYPE: DNA
<213> ORGANISM: Artificial Sequence
<220> FEATURE:
<223> OTHER INFORMATION: Fused Polypeptide (FuG-A)
<220> FEATURE:
<221> NAME/KEY: CDS
<222> LOCATION: (1)..(1524)

<400> SEQUENCE: 5
```

| | | | | | | | | | | | | | | | | |
|---|---|---|---|---|---|---|---|---|---|---|---|---|---|---|---|---|
| atg | gtt | ccg | cag | gtt | ctt | ttg | ttt | gta | ctc | ctt | ctg | ggt | ttt | tcg | ttg | 48 |
| Met | Val | Pro | Gln | Val | Leu | Leu | Phe | Val | Leu | Leu | Leu | Gly | Phe | Ser | Leu | |
| 1 | | | | 5 | | | | | 10 | | | | | 15 | | |
| tgt | ttc | ggg | aag | ttc | ccc | att | tac | acg | ata | cca | gac | gaa | ctt | ggt | ccc | 96 |
| Cys | Phe | Gly | Lys | Phe | Pro | Ile | Tyr | Thr | Ile | Pro | Asp | Glu | Leu | Gly | Pro | |
| | | | 20 | | | | | 25 | | | | | 30 | | | |
| tgg | agc | cct | att | gac | ata | cac | cat | ctc | agc | tgt | cca | aat | aac | ctg | gtt | 144 |
| Trp | Ser | Pro | Ile | Asp | Ile | His | His | Leu | Ser | Cys | Pro | Asn | Asn | Leu | Val | |
| | | 35 | | | | | 40 | | | | | 45 | | | | |
| gtg | gag | gat | gaa | gga | tgt | acc | aac | ctg | tcc | gag | ttc | tcc | tac | atg | gaa | 192 |
| Val | Glu | Asp | Glu | Gly | Cys | Thr | Asn | Leu | Ser | Glu | Phe | Ser | Tyr | Met | Glu | |
| 50 | | | | | 55 | | | | | 60 | | | | | | |
| ctc | aaa | gtg | gga | tac | atc | tca | gcc | atc | aaa | gtg | aac | ggg | ttc | act | tgc | 240 |
| Leu | Lys | Val | Gly | Tyr | Ile | Ser | Ala | Ile | Lys | Val | Asn | Gly | Phe | Thr | Cys | |
| 65 | | | | | 70 | | | | | 75 | | | | | 80 | |
| aca | ggt | gtt | gtg | aca | gag | gca | gag | acc | tac | acc | aac | ttt | gtt | ggt | tat | 288 |
| Thr | Gly | Val | Val | Thr | Glu | Ala | Glu | Thr | Tyr | Thr | Asn | Phe | Val | Gly | Tyr | |
| | | | | 85 | | | | | 90 | | | | | 95 | | |
| gtc | aca | acc | aca | ttc | aag | aga | aag | cat | ttc | cgc | ccc | acc | cca | gac | gca | 336 |
| Val | Thr | Thr | Thr | Phe | Lys | Arg | Lys | His | Phe | Arg | Pro | Thr | Pro | Asp | Ala | |
| | | | 100 | | | | | 105 | | | | | 110 | | | |
| tgt | aga | gcc | gcg | tat | aac | tgg | aag | atg | gcc | ggt | gac | ccc | aga | tat | gaa | 384 |
| Cys | Arg | Ala | Ala | Tyr | Asn | Trp | Lys | Met | Ala | Gly | Asp | Pro | Arg | Tyr | Glu | |
| | | 115 | | | | | 120 | | | | | 125 | | | | |
| gag | tcc | cta | cac | aat | cca | tac | ccc | gac | tac | cac | tgg | ctt | cga | act | gta | 432 |
| Glu | Ser | Leu | His | Asn | Pro | Tyr | Pro | Asp | Tyr | His | Trp | Leu | Arg | Thr | Val | |
| | | 130 | | | | | 135 | | | | | 140 | | | | |
| aga | acc | acc | aaa | gag | tcc | ctc | att | atc | ata | tcc | cca | agt | gtg | aca | gat | 480 |
| Arg | Thr | Thr | Lys | Glu | Ser | Leu | Ile | Ile | Ile | Ser | Pro | Ser | Val | Thr | Asp | |
| 145 | | | | | 150 | | | | | 155 | | | | | 160 | |
| ttg | gac | cca | tat | gac | aaa | tcc | ctt | cac | tca | agg | gtc | ttc | cct | ggc | gga | 528 |
| Leu | Asp | Pro | Tyr | Asp | Lys | Ser | Leu | His | Ser | Arg | Val | Phe | Pro | Gly | Gly | |

|   |   |   |   |   |   |   |   |   |   |   |   |   |   |   |   |     |
|---|---|---|---|---|---|---|---|---|---|---|---|---|---|---|---|-----|
| Leu | Asp | Pro | Tyr | Asp | Lys | Ser | Leu | His | Ser | Arg | Val | Phe | Pro | Gly | Gly |     |
|   |   |   |   |   | 165 |   |   |   | 170 |   |   |   | 175 |   |   |     |

```
aag tgc tca gga ata acg gtg tcc tct acc tac tgc tca act aac cat         576
Lys Cys Ser Gly Ile Thr Val Ser Ser Thr Tyr Cys Ser Thr Asn His
            180                 185                 190 gat tac acc att tgg atg ccc gag aat ccg aga cca agg aca cct tgt         624
Asp Tyr Thr Ile Trp Met Pro Glu Asn Pro Arg Pro Arg Thr Pro Cys
        195                 200                 205 gac att ttt acc aat agc aga ggg aag aga gca tcc aac ggg aac aag         672
Asp Ile Phe Thr Asn Ser Arg Gly Lys Arg Ala Ser Asn Gly Asn Lys
210                 215                 220 act tgc ggc ttt gtg gat gaa aga ggc ctg tat aag tct cta aaa gga         720
Thr Cys Gly Phe Val Asp Glu Arg Gly Leu Tyr Lys Ser Leu Lys Gly
225                 230                 235                 240 gca tgc agg ctc aag tta tgt gga gtt ctt gga ctt aga ctt atg gat         768
Ala Cys Arg Leu Lys Leu Cys Gly Val Leu Gly Leu Arg Leu Met Asp
            245                 250                 255 gga aca tgg gtc gcg atg caa aca tca gat gag acc aaa tgg tgc cct         816
Gly Thr Trp Val Ala Met Gln Thr Ser Asp Glu Thr Lys Trp Cys Pro
        260                 265                 270 cca gat cag ttg gtg aat ttg cac gac ttt cgc tca gac gag atc gag         864
Pro Asp Gln Leu Val Asn Leu His Asp Phe Arg Ser Asp Glu Ile Glu
275                 280                 285 cat ctc gtt gtg gag gag tta gtt aag aaa aga gag gaa tgt ctg gat         912
His Leu Val Val Glu Glu Leu Val Lys Lys Arg Glu Glu Cys Leu Asp
            290                 295                 300 gca tta gag tcc atc atg acc acc aag tca gta agt ttc aga cgt ctc         960
Ala Leu Glu Ser Ile Met Thr Thr Lys Ser Val Ser Phe Arg Arg Leu
305                 310                 315                 320 agt cac ctg aga aaa ctt gtc cca ggg ttt gga aaa gca tat acc ata        1008
Ser His Leu Arg Lys Leu Val Pro Gly Phe Gly Lys Ala Tyr Thr Ile
            325                 330                 335 ttc aac aaa acc ttg atg gag gct gat gct cac tac aag tca gtc cgg        1056
Phe Asn Lys Thr Leu Met Glu Ala Asp Ala His Tyr Lys Ser Val Arg
        340                 345                 350 acc tgg aat gag atc atc ccc tca aaa ggg tgt ttg aaa gtt gga gga        1104
Thr Trp Asn Glu Ile Ile Pro Ser Lys Gly Cys Leu Lys Val Gly Gly
355                 360                 365 agg tgc cat cct cat gtg aac ggg gtg ttt ttc aat ggt ata ata tta        1152
Arg Cys His Pro His Val Asn Gly Val Phe Phe Asn Gly Ile Ile Leu
370                 375                 380 ggg cct gac gac cat gtc cta atc cca gag atg caa tca tcc ctc ctc        1200
Gly Pro Asp Asp His Val Leu Ile Pro Glu Met Gln Ser Ser Leu Leu
385                 390                 395                 400 cag caa cat atg gag ttg ttg gaa tct tca gtt atc ccc ctg atg cac        1248
Gln Gln His Met Glu Leu Leu Glu Ser Ser Val Ile Pro Leu Met His
            405                 410                 415 ccc ctg gca gac cct tct aca gtt ttc aaa gaa ggt gat gag gct gag        1296
Pro Leu Ala Asp Pro Ser Thr Val Phe Lys Glu Gly Asp Glu Ala Glu
        420                 425                 430 gat ttt gtt gaa gtt cac ctc ccc gat gtg tac aaa cag atc tca ggg        1344
Asp Phe Val Glu Val His Leu Pro Asp Val Tyr Lys Gln Ile Ser Gly
435                 440                 445 gtt gac ctg ggt ctc ccg aac tgg gga aag agc tct att gcc tct ttt        1392
Val Asp Leu Gly Leu Pro Asn Trp Gly Lys Ser Ser Ile Ala Ser Phe
            450                 455                 460 ttc ttt atc ata ggg tta atc att gga cta ttc ttg gtt ctc cga gtt        1440
Phe Phe Ile Ile Gly Leu Ile Ile Gly Leu Phe Leu Val Leu Arg Val
465                 470                 475                 480
```

```
ggt atc cat ctt tgc att aaa tta aag cac acc aag aaa aga cag att     1488
Gly Ile His Leu Cys Ile Lys Leu Lys His Thr Lys Lys Arg Gln Ile
                485                 490                 495 tat aca gac ata gag atg aac cga ctt gga aag taa                    1524
Tyr Thr Asp Ile Glu Met Asn Arg Leu Gly Lys
                500                 505

<210> SEQ ID NO 6
<211> LENGTH: 507
<212> TYPE: PRT
<213> ORGANISM: Artificial Sequence
<220> FEATURE:
<223> OTHER INFORMATION: Fused Polypeptide (FuG-A)

<400> SEQUENCE: 6

Met Val Pro Gln Val Leu Leu Phe Val Leu Leu Leu Gly Phe Ser Leu
1               5                   10                  15

Cys Phe Gly Lys Phe Pro Ile Tyr Thr Ile Pro Asp Glu Leu Gly Pro
                20                  25                  30

Trp Ser Pro Ile Asp Ile His His Leu Ser Cys Pro Asn Asn Leu Val
            35                  40                  45

Val Glu Asp Glu Gly Cys Thr Asn Leu Ser Glu Phe Ser Tyr Met Glu
        50                  55                  60

Leu Lys Val Gly Tyr Ile Ser Ala Ile Lys Val Asn Gly Phe Thr Cys
65                  70                  75                  80

Thr Gly Val Val Thr Glu Ala Glu Thr Tyr Thr Asn Phe Val Gly Tyr
                85                  90                  95

Val Thr Thr Thr Phe Lys Arg Lys His Phe Arg Pro Thr Pro Asp Ala
                100                 105                 110

Cys Arg Ala Ala Tyr Asn Trp Lys Met Ala Gly Asp Pro Arg Tyr Glu
            115                 120                 125

Glu Ser Leu His Asn Pro Tyr Pro Asp Tyr His Trp Leu Arg Thr Val
        130                 135                 140

Arg Thr Thr Lys Glu Ser Leu Ile Ile Ile Ser Pro Ser Val Thr Asp
145                 150                 155                 160

Leu Asp Pro Tyr Asp Lys Ser Leu His Ser Arg Val Phe Pro Gly Gly
                165                 170                 175

Lys Cys Ser Gly Ile Thr Val Ser Ser Thr Tyr Cys Ser Thr Asn His
            180                 185                 190

Asp Tyr Thr Ile Trp Met Pro Glu Asn Pro Arg Pro Arg Thr Pro Cys
        195                 200                 205

Asp Ile Phe Thr Asn Ser Arg Gly Lys Arg Ala Ser Asn Gly Asn Lys
210                 215                 220

Thr Cys Gly Phe Val Asp Glu Arg Gly Leu Tyr Lys Ser Leu Lys Gly
225                 230                 235                 240

Ala Cys Arg Leu Lys Leu Cys Gly Val Leu Gly Leu Arg Leu Met Asp
                245                 250                 255

Gly Thr Trp Val Ala Met Gln Thr Ser Asp Glu Thr Lys Trp Cys Pro
            260                 265                 270

Pro Asp Gln Leu Val Asn Leu His Asp Phe Arg Ser Asp Glu Ile Glu
        275                 280                 285

His Leu Val Val Glu Glu Leu Val Lys Lys Arg Glu Glu Cys Leu Asp
    290                 295                 300

Ala Leu Glu Ser Ile Met Thr Thr Lys Ser Val Ser Phe Arg Arg Leu
305                 310                 315                 320

Ser His Leu Arg Lys Leu Val Pro Gly Phe Gly Lys Ala Tyr Thr Ile
```

-continued

```
                325                 330                 335

Phe Asn Lys Thr Leu Met Glu Ala Asp Ala His Tyr Lys Ser Val Arg
            340                 345                 350
Thr Trp Asn Glu Ile Ile Pro Ser Lys Gly Cys Leu Lys Val Gly Gly
        355                 360                 365

Arg Cys His Pro His Val Asn Gly Val Phe Phe Asn Gly Ile Ile Leu
    370                 375                 380

Gly Pro Asp Asp His Val Leu Ile Pro Glu Met Gln Ser Ser Leu Leu
385                 390                 395                 400

Gln Gln His Met Glu Leu Leu Glu Ser Ser Val Ile Pro Leu Met His
                405                 410                 415
Pro Leu Ala Asp Pro Ser Thr Val Phe Lys Glu Gly Asp Glu Ala Glu
            420                 425                 430
Asp Phe Val Glu Val His Leu Pro Asp Val Tyr Lys Gln Ile Ser Gly
        435                 440                 445

Val Asp Leu Gly Leu Pro Asn Trp Gly Lys Ser Ser Ile Ala Ser Phe
    450                 455                 460

Phe Phe Ile Ile Gly Leu Ile Ile Gly Leu Phe Leu Val Leu Arg Val
465                 470                 475                 480
Gly Ile His Leu Cys Ile Lys Leu Lys His Thr Lys Lys Arg Gln Ile
                485                 490                 495
Tyr Thr Asp Ile Glu Met Asn Arg Leu Gly Lys
            500                 505
```